(12) United States Patent
Furman et al.

(10) Patent No.: US 9,010,320 B2
(45) Date of Patent: Apr. 21, 2015

(54) MANUALLY ARTICULATED INTUBATION STYLET, INTUBATION DEVICE AND INTUBATION METHOD

(71) Applicant: Furman Medical LLC, West Pueblo, CO (US)

(72) Inventors: William Furman, Denver, CO (US); Francis Furman, Lakewood, CO (US); Matthew Furman, West Pueblo, CO (US)

(73) Assignee: Furman Medical LLC, Pueblo, CO (US)

( * ) Notice: Subject to any disclaimer, the term of this patent is extended or adjusted under 35 U.S.C. 154(b) by 52 days.

(21) Appl. No.: 13/794,121

(22) Filed: Mar. 11, 2013

(65) Prior Publication Data

US 2013/0255671 A1    Oct. 3, 2013

Related U.S. Application Data

(60) Provisional application No. 61/609,442, filed on Mar. 12, 2012.

(51) Int. Cl.
| | | |
|---|---|---|
| *A61M 16/00* | (2006.01) | |
| *A61F 11/00* | (2006.01) | |
| *A61M 16/04* | (2006.01) | |

(52) U.S. Cl.
CPC .................. *A61M 16/0488* (2013.01)

(58) Field of Classification Search
USPC .................................................. 128/200.26
See application file for complete search history.

(56) References Cited

U.S. PATENT DOCUMENTS

| | | | |
|---|---|---|---|
| 2,541,402 A | | 2/1951 | Caine |
| 3,470,876 A | | 10/1969 | Barchilon |
| 3,802,440 A | * | 4/1974 | Salem et al. ............ 128/200.26 |
| 4,150,676 A | | 4/1979 | Jackson |
| 4,329,983 A | | 5/1982 | Fletcher |
| 4,353,358 A | | 10/1982 | Emerson |
| 4,589,410 A | | 5/1986 | Miller |
| 4,613,323 A | | 9/1986 | Norton et al. |
| 4,685,457 A | | 8/1987 | Donenfeld |
| 5,163,941 A | | 11/1992 | Garth et al. |
| 5,203,320 A | | 4/1993 | Augustine |
| 5,231,989 A | | 8/1993 | Middleman et al. |
| 5,235,970 A | | 8/1993 | Augustine |
| 5,255,668 A | | 10/1993 | Umeda |
| 5,259,377 A | | 11/1993 | Schroeder |
| 5,306,245 A | | 4/1994 | Heaven |
| 5,441,483 A | * | 8/1995 | Avitall ........................ 604/95.05 |
| 5,467,763 A | * | 11/1995 | McMahon et al. ............ 600/201 |
| 5,643,221 A | | 7/1997 | Bullard |

(Continued)

*Primary Examiner* — Tuan V Nguyen
(74) *Attorney, Agent, or Firm* — Marsh Fischmann & Bregyfogle LLP

(57) ABSTRACT

Apparatuses useful in and methods for positioning of an endotracheal tube within an airway by allowing manual articulation of the endotracheal tube while a patient is being intubated. The apparatuses and methods are of particular use in intubating patients with unique anatomical conditions that make standard stylets inadequate for intubation. In one embodiment, an apparatus may comprise a stylet having a first end and a second end, with the second end of the stylet being insertable within a lumen of the endotracheal tube. First and second articulatable portions of the stylet may be independently articulated into respective primary and secondary arcuations to bend the endotracheal tube in conformance therewith as desired during the intubation procedure.

35 Claims, 7 Drawing Sheets

(56) References Cited

U.S. PATENT DOCUMENTS

| | | |
|---|---|---|
| 5,791,338 A | 8/1998 | Merchant et al. |
| 6,169,916 B1 | 1/2001 | West |
| 6,183,435 B1 | 2/2001 | Bumbalough et al. |
| 6,183,463 B1 | 2/2001 | Webster, Jr. |
| 6,224,587 B1 | 5/2001 | Gibson |
| 6,238,389 B1 | 5/2001 | Paddock et al. |
| 6,251,092 B1 | 6/2001 | Qin et al. |
| 6,270,476 B1 | 8/2001 | Santoianni et al. |
| 6,321,749 B1 | 11/2001 | Toti et al. |
| 6,582,536 B2 | 6/2003 | Shimada |
| 7,137,990 B2 | 11/2006 | Hebert et al. |
| 7,243,653 B2 | 7/2007 | Nelson |
| D650,901 S | 12/2011 | Ghosh |
| 2001/0037084 A1 | 11/2001 | Nardeo |
| 2001/0039413 A1 | 11/2001 | Bowe |
| 2001/0049518 A1 | 12/2001 | Hoch |
| 2003/0109861 A1 | 6/2003 | Shimada |
| 2011/0265789 A1* | 11/2011 | Gabriel .................... 128/200.26 |
| 2012/0073572 A1* | 3/2012 | Li ............................. 128/200.26 |

* cited by examiner

US 9,010,320 B2

MANUALLY ARTICULATED INTUBATION STYLET, INTUBATION DEVICE AND INTUBATION METHOD

RELATED APPLICATION INFORMATION

This application claims priority from U.S. Provisional Application Ser. No. 61/609,442, entitled "MANUALLY ARTICULATED INTUBATION STYLET, INTUBATION DEVICE AND INTUBATION METHOD" filed on Mar. 12, 2012, which is incorporated by reference herein in its entirety.

FIELD OF THE INVENTION

The present invention relates generally to endotracheal intubation, and more particularly to apparatuses and methods useful in the positioning of an endotracheal tube within the airway of a patient.

BACKGROUND OF THE INVENTION

Anesthesiologists and other medical care providers are often required to intubate patients in order to provide an adequate airway for the patient during receipt of medical care. One manner of intubating a patient involves positioning an endotracheal tube into the patient's trachea.

Various implements can be used to assist in the process of positioning endotracheal tubes including, for example, Macintosh blades, Miller blades and intubation stylets. Macintosh blades generally comprise a curved-bladed implement and are typically used to lift a patient's vallecula out of the way providing the medical care provider a better view of the patient's airway. Miller blades generally comprise a straight-bladed implement and are typically used to trap the patient's epiglottis to better expose the patient's glottis and vocal cords. An intubation stylet may be inserted within the lumen of an endotracheal tube. The stylet may be used with or without other implements (e.g. Macintosh blades and/or Miller blades) to help guide the tube into the patient's trachea. After the endotracheal tube is properly positioned in the patient's airway, the stylet is removed from the lumen of the endotracheal tube allowing a ventilator or the like to be attached to the tube to ventilate the patient.

Despite the availability of various stylets and other implements, the insertion of endotracheal tubes can be difficult even for skilled providers, particularly in patient's having anterior tracheas and other conditions that make it challenging to guide the distal end of the endotracheal tube past the vocal cords and into the trachea. In some instances where an endotracheal tube cannot be properly positioned at all or within a timely enough manner, the patient may need to have a tracheotomy.

SUMMARY OF THE INVENTION

Accordingly, apparatuses and methods useful in the positioning of an endotracheal tube within an airway during an intubation procedure are provided. The apparatuses and methods described herein are useful in assisting the intubation of patients in both routine and emergency procedures. The apparatuses and methods described herein are particularly suited for intubating a human patient. However, the apparatuses and methods described herein may also be applicable to the intubation of non-human patients as well.

The apparatuses and methods provide, for example, the ability to more readily insert an endotracheal tube into the trachea of a patient and desirably avoid the need for a tracheotomy. The apparatuses and methods further provide, for example, the ability to bend the endotracheal tube in more than one direction while the tube is being positioned in a patient's airway. The ability to bend the endotracheal tube in two directions (e.g. a clockwise bend over a middle portion of the tube and a counter-clockwise bend over a distal end portion end of the tube) helps a medical care provider advance the distal end of the tube past the vocal cords and into the trachea of the patient, particularly in a patient having an anterior trachea or other challenging anatomy. The apparatuses and methods further provide, for example, the ability to bend one portion of the endotracheal tube (e.g. the distal end portion) in one direction independent of a different portion of the endotracheal tube (e.g. a portion preceding the distal end portion) being bent in another direction. The ability to independently bend different portions of the tube affords the medical provider the ability to readily manipulate the endotracheal tube as needed to accomplish positioning of the tube in a patient with challenging anatomy.

Advantages of the apparatuses and methods described herein further include, without limitation, the ability to control the shape of an endotracheal tube, the ability to respond to unique anatomical differences in trachea location and shape, and the ability to utilize a disposable stylet while continuing to use other portions of the apparatus.

These and other features and advantages are achieved by various aspects of the apparatuses and methods described herein. In one aspect, an apparatus useful in the positioning of an endotracheal tube within an airway comprises a stylet having a first end and a second end. The second end of the stylet may be insertable within a lumen of the endotracheal tube such that at least a portion of a longitudinal extent of the stylet is received within the lumen of the endotracheal tube. A first filament may extend substantially parallel with a longitudinal axis of the stylet. The first filament may be connected to the stylet at a first location between the first and second ends. A second filament may extend substantially parallel with the longitudinal axis of the stylet. The second filament may be connected to the stylet at a second location farther from the first end than the first location. A first tensioning mechanism may be operable to put the first filament under tension to articulate the stylet into a primary arcuation that may extend from the first location toward the first end. A second tensioning mechanism may be operable to put the second filament under tension to articulate the stylet into a secondary arcuation that may extend from the second location toward the first location.

In another aspect, an apparatus useful in the positioning of an endotracheal tube within an airway may comprise a stylet having a first end and a second end. The second end of the stylet may be insertable within a lumen of the endotracheal tube such that at least a portion of a longitudinal extent of the stylet is received within the lumen of the endotracheal tube. The stylet may comprise at least a first articulatable portion extending toward the first end from a first location along a longitudinal extent of the stylet and a second articulatable portion extending toward the first location from a second location along the longitudinal extent of the stylet farther from the first end than the first location. The first articulatable portion of the stylet may be articulatable into a primary arcuation and the second articulatable portion of the stylet may be articulatable into a secondary arcuation. In this regard, the first and second articulatable portions of the stylet may be independently articulatable into respective primary and secondary arcuations.

In a further aspect, a method for positioning an endotracheal tube within an airway may comprise coupling a first end of a stylet with a handle body including first and second articulating mechanisms. The stylet may include a first articulatable portion extending toward the first end from a first location along a longitudinal extent of the stylet and a second articulatable portion extending toward the first location from a second location along the longitudinal extent of the stylet farther from the first end than the first location. In this regard, the first and second articulating mechanisms may be independently operable. The method may further comprise inserting a second end of the stylet within a lumen of the endotracheal tube such that at least a portion of the longitudinal extent of the stylet is received within the lumen of the endotracheal tube. The method may additionally comprise, concurrent with positioning the endotracheal tube within the airway, operating the first articulating mechanism to articulate the first portion of the stylet into a primary arcuation and/or operating the second articulating mechanism to articulate the second portion of the stylet into a secondary arcuation.

Various apparatuses and methodologies are provided herein. Such apparatuses and methodologies may be employed separately and in combination. Various refinements exist of the features noted in relation to the various aspects, and further features may also be incorporated in the various aspects. These refinements and additional features may exist individually or in any combination, and various features of the various aspects may be combined. These and other aspects and advantages will be apparent upon review of the following Detailed Description when taken in conjunction with the accompanying figures.

DETAILED DESCRIPTION

Figure 1:
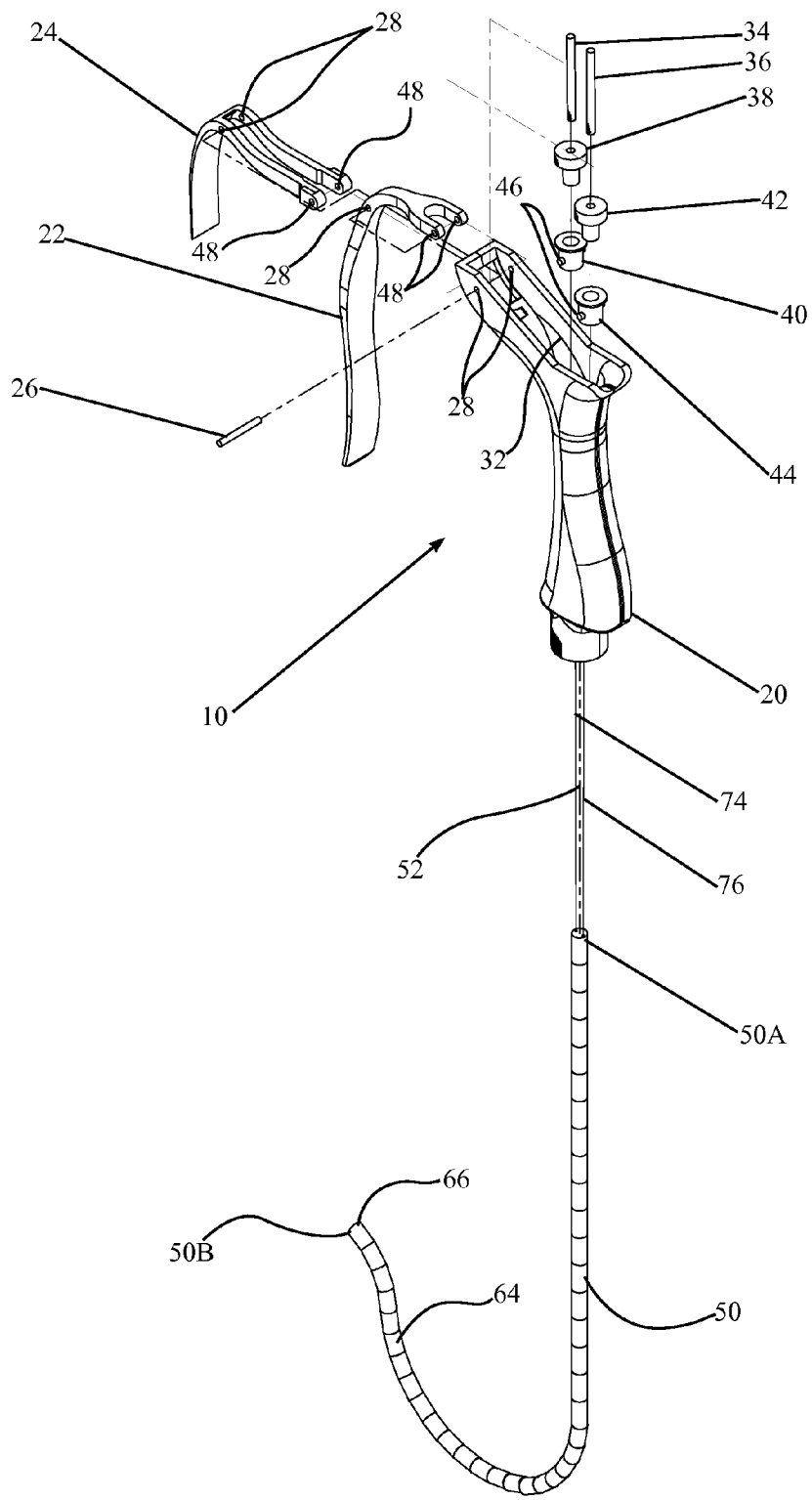
FIG. 1 is a perspective exploded view of one embodiment of a manually articulatable intubation apparatus.

FIG. 1 shows one embodiment of a manually articulatable intubation apparatus 10. The manually articulatable intubation apparatus 10 includes a handle body 20 that may be held in an upright position as illustrated. The manually articulatable intubation apparatus 10 also includes an articulating stylet 50. The stylet 50 includes a first end 50A proximal to the handle body 20 and a second end 50B distal from the handle body 20. When assembled, the first end 50A of the stylet may be seated against a stylet seating surface 20A (not shown in FIG. 1) formed at the bottom of a stylet changing opening 30 (not shown in FIG. 1) in the base of the handle body 20. The stylet seating surface 20A and stylet changing opening 30 may be seen in FIG. 7.

A major handle lever 22 and a minor handle lever 24 mount freely to the handle body 20 on an axle pin 26. Major handle lever 22 may also be referred to herein as first lever 22 and minor handle lever 24 may also be referred to herein as second lever 24. Axle pin 26 is received in axle pin holes 28 formed in the handle body 20, the major handle lever 22 and the minor handle lever 24 to mount the major and minor handle levers 22, 24 on the handle body 20 in a pivotable manner about a fulcrum provided by the axle pin 26. In other embodiments, the major and minor handle levers 22, 24 may be pivotably mounted on the handle body 20 in other manners including, for example, by separate axle pins.

A first filament 74 and a second filament 76 extend from the first end 50A of the stylet 50 and through the stylet changing opening 30 (shown in FIG. 7) into the open interior of handle body 20. The first filament 74 also extends parallel with a longitudinal axis 52 of the stylet 50 through a first longitudinal passageway 54 formed within the stylet 50 to a first location 64 along a longitudinal extent of the stylet 50. The first filament 74 is connected to the stylet 50 at the first location 64. The first filament 74 may be connected with the stylet 50 at the first location 64 in a variety of manners including, for example, by soldering the first filament 74 to the stylet 50 at the first location 64. In this regard, the first filament 74 may comprise a metallic wire (e.g. a piano wire) and the stylet 50 may be comprised of metal at the first location 64. The second filament 76 also extends parallel with the longitudinal axis 52 of the stylet 50 through a second longitudinal passageway 56 formed within the stylet 50 to a second location 66 along the longitudinal extent of the stylet 50. The second filament 76 is connected to the stylet 50 at the second location 66. The second filament 76 may be connected with the stylet 50 at the second location 66 in a variety of manners including, for example, by soldering the second filament 76 to the stylet 50 at the second location 66. In this regard, the second filament 76 may comprise a metallic wire (e.g. a piano wire) and the stylet 50 may be comprised of metal at the second location 66. In other embodiments, the first and second filaments 74, 76 may comprise materials other than metallic wire and/or may be connected to the stylet 50 at the respective first and second locations 64, 66 thereof in manners other than soldering.

The first and second filaments 74, 76 exit the interior of the handle body 20 through a top slot 32 formed in an upper portion of the handle body 20. The first filament 74 is connected to a first threaded tensioning screw 34 and the second filament 76 is connected to a second threaded tensioning screw 36. The first filament 74 may be connected with the first threaded tensioning screw 34 in a variety of manners including, for example, by soldering the first filament 74 to the bottom of the first threaded tensioning screw 34. In this regard, the first filament 74 may comprise a metallic wire (e.g. piano wire) and the first threaded tensioning screw 34 may be comprised of metal. The second filament 76 may be connected with the second threaded tensioning screw 36 in a variety of manners including, for example, by soldering the second filament 76 to the second threaded tensioning screw 36. In this regard, the second filament 76 may comprise a metallic wire (e.g. piano wire) and the second threaded tensioning screw 36 may be comprised of metal. In other embodiments, the first and second threaded tensioning screws 34, 36 may be comprised of non-metallic materials, and/or the first and second filaments 74, 76 may comprise materials other than metallic wire and/or may be connected to the respective first and second threaded tensioning screws 34, 66 in manners other than soldering. Regardless of the material comprising the first and second filaments 74, 76, the first and second filaments 74, 76 may desirably have sufficient yield strength in order to avoid undesirable deformation during use of the manually articulatable intubation apparatus. In this regard, the first and second filaments 74, 76 may, for example, have a yield strength of about 20,000 pounds per square inch or greater.

The first threaded tensioning screw 34 is threaded into a first tensioning thumb nut 38. The first tensioning thumb nut 38 sits freely in a first gimbal 40. The first gimbal 40 is pinned freely to the major handle lever 22 via laterally extending gimbal pins 46 received in gimbal pin holes 48 formed in the major handle lever 22. In this regard, the first threaded tensioning screw 34, first tensioning thumb nut 38 and first gimbal 40 may together comprise a first gimbal and tension adjustment assembly connecting the first filament 74 to the major handle lever 22. The second threaded tensioning screw 36 is threaded into a second tensioning thumb nut 42. The second tensioning thumb nut 42 sits freely in a second gimbal 44. The second gimbal 44 is pinned freely to the minor handle lever 24 via laterally extending gimbal pins 46 received in gimbal pin holes 48 formed in the minor handle lever 24. In this regard, the second threaded tensioning screw 36, second tensioning thumb nut 42 and second gimbal 44 may together comprise a second gimbal and tension adjustment assembly connecting the second filament 76 to the minor handle 20.

The first and second gimbal and tensioning adjustment assemblies allow for an initial tension in the first filament 74 and/or the second filament 76 to be adjusted independently of one another. The first tensioning thumb nut 38 sits freely in the first gimbal 40 allowing the first tensioning thumb nut 38 to be turned in order to adjust an initial tension on the first filament 74. For example, as the first tensioning thumb nut 38 is turned in one direction (e.g., clockwise), threads on the first tensioning thumb nut 38 engage threads on the first threaded tensioning screw 34 moving the first threaded tensioning screw 34 up relative to the major handle lever 22 thereby increasing an initial tension in the first filament 74 between the first gimbal 40 and the first location 64 of the stylet 50, and as the first tensioning thumb nut 38 is turned in an opposite direction (e.g., counter-clockwise), threads on the first tensioning thumb nut 38 engage threads on the first threaded tensioning screw 34 moving the first threaded tensioning screw 34 down relative to the major handle lever 22 thereby decreasing an initial tension in the first filament 74 between the first gimbal 40 and the first location 64 of the stylet 50. The second tensioning thumb nut 42 sits freely in the second gimbal 44 allowing the second tensioning thumb nut 42 to be turned to adjust an initial tension on the second filament 76. For example, as the second tensioning thumb nut 42 is turned in one direction (e.g. clockwise), threads on the second tensioning thumb nut 42 engage threads on the second threaded tensioning screw 36 moving the second threaded tensioning screw 36 up relative to the minor handle lever 24 thereby increasing an initial tension in the second filament 76 between the second gimbal 44 and the second location 66 of the stylet 50, and as the second tensioning thumb nut 42 is turned in an opposite direction (e.g. counter-clockwise), threads on the second tensioning thumb nut 42 engage threads on the second threaded tensioning screw 36 moving the second threaded tensioning screw 36 down relative to the minor handle lever 24 thereby decreasing an initial tension in the second filament 76 between the second gimbal 44 and the second location 66 of the stylet 50. In this regard, the first tensioning thumb nut 38 and the second tensioning thumb nut 42 may each include a knurled texture on outside surfaces thereof to facilitate gripping of the tensioning thumb nuts 38, 42 when turning.

The first and second gimbal and tensioning adjustment assemblies also help reduce lateral forces on the first and second filaments 74, 76 when the major and minor handle levers 22, 24 are pivoted on the axle pin 26. In this regard, the first and second gimbals 40, 44 pivot on their gimbal pins 46 relative to the respective major and minor handle levers 22, 24 as the respective major and minor handle levers 22, 24 are pivoted. This allows the first and second gimbal and tensioning adjustment assemblies to move up and down in response to pivoting of the major and/or minor handle levers 22, 24 while maintaining the first and second threaded tensioning screws 34, 36 to which the first and second filaments 74, 76 are respectively connected to maintain a generally vertical orientation thereby minimizing lateral forces on the first and second filaments 74, 76, particularly at the point of connection to the first and second threaded tensioning screws 34, 36.

The handle body 20 of the manually articulated intubation apparatus 10 may be shaped and contoured such that the handle body 20 rests comfortably against the palm of a single hand, right or left, allowing the major handle lever 22 and/or the minor handle lever 24 to be readily pulled by the fingers against the handle body 20 thereby pivoting on the axle pin 26. The handle body 20 may be constructed of a sufficiently rigid material so that the handle body 20 does not excessively deform during use of the manually articulated intubation apparatus 10, such as, for example, a rigid plastic or a metal (e.g. stainless steel).

The portions of the major and minor handle levers 22, 24 engaged by the fingers to pull the major and minor handle levers 22 toward the handle body 20 may be sufficiently long to provide leverage when pulled toward the handle body 20 so that the first and second filaments 74, 76 can be comfortably put under sufficient tension. The minor handle lever 24 may be provided with a sufficiently larger radius curved configuration in comparison to the major handle lever 22 to allow the minor handle lever 24 to be pulled toward the tighter radius curved configuration of the major handle lever 24 without requiring movement of the major handle lever 22 toward the handle body 20. The major and minor handles 22, 24 may be constructed of a sufficiently rigid material so that the major and minor handles 22, 24 do not excessively flex during use of the manually articulated intubation apparatus 10, such as, for example, any plastic or metal sufficiently strong and rigid to maintain their contour during use.

The first and second threaded tensioning screws 34, 36 may be made from a material sufficiently rigid enough to maintain their threads while under tension such as, for example, a metal (e.g., steel). The first and second tensioning thumb nuts 38, 42 may be made of any material sufficiently rigid to maintain their outer surface knurl texture and their threads such as, for example a metal (e.g. steel). The first and second gimbals 40, 44 may be made from any sufficiently strong material to withstand forces applied thereto by the initial tension on the first and second filaments 74, 76 and upon pivoting of the major and minor handles 22, 24 such as, for example, a metal (e.g., steel). The axle pin 26 may be made of a material sufficiently hard and strong (e.g. a metal) to withstand repeated rotation of the major and minor handle levers 22, 24 as well as the forces applied to the axle pin 26 as the fulcrum about which the major and minor handle levers 22, 24 pivot.

The second end 50A of the articulating stylet 50 is insertable within the lumen of an endotracheal tube. The articulating stylet 50 has a sufficient longitudinal extent or length such that when fully inserted within the lumen of an endotracheal tube, the second end 50B of the stylet 50 reaches the internal tip of a standard endotracheal tube, and not beyond. However, it may be possible to utilize the stylet 50 with an endotracheal tube that is shorter than standard length by not fully inserting the stylet 50 into the lumen of the shorter endotracheal tube or by having the second end 50B of the stylet 50 extend beyond the internal tip of the shorter endotracheal tube. It may also be possible to utilize the stylet 50 with an endotracheal tube that is longer than standard length by having second end 50B of the stylet 50 extend not quite to the internal tip of the longer endotracheal tube. Furthermore, it is possible that different length stylets 50 may be provided for use with different length endotracheal tubes. The articulating stylet 50 can be made of any material sufficiently hard and strong to withstand the compressive forces applied thereto by tension in the first and second filaments 74, 76 such as, for example, a plastic material (e.g., DELRIN® available from DuPont corporation).

Referring now in particular to FIGS. 2, 3, 4, and 5, the manually articulatable intubation apparatus 10 is shown with the articulating stylet 50 in various stages of articulation. An exemplary endotracheal tube 80 represented by the dashed lines in FIGS. 2, 3, 4 and 5 is shown with the stylet 50 being disposed within a lumen of the endotracheal tube 80. Various features that may be included in an endotracheal tube such as, for example, a cuff and an inflation tube, are not illustrated as part of the endotracheal tube 80 shown in the figures.

Figure 2:
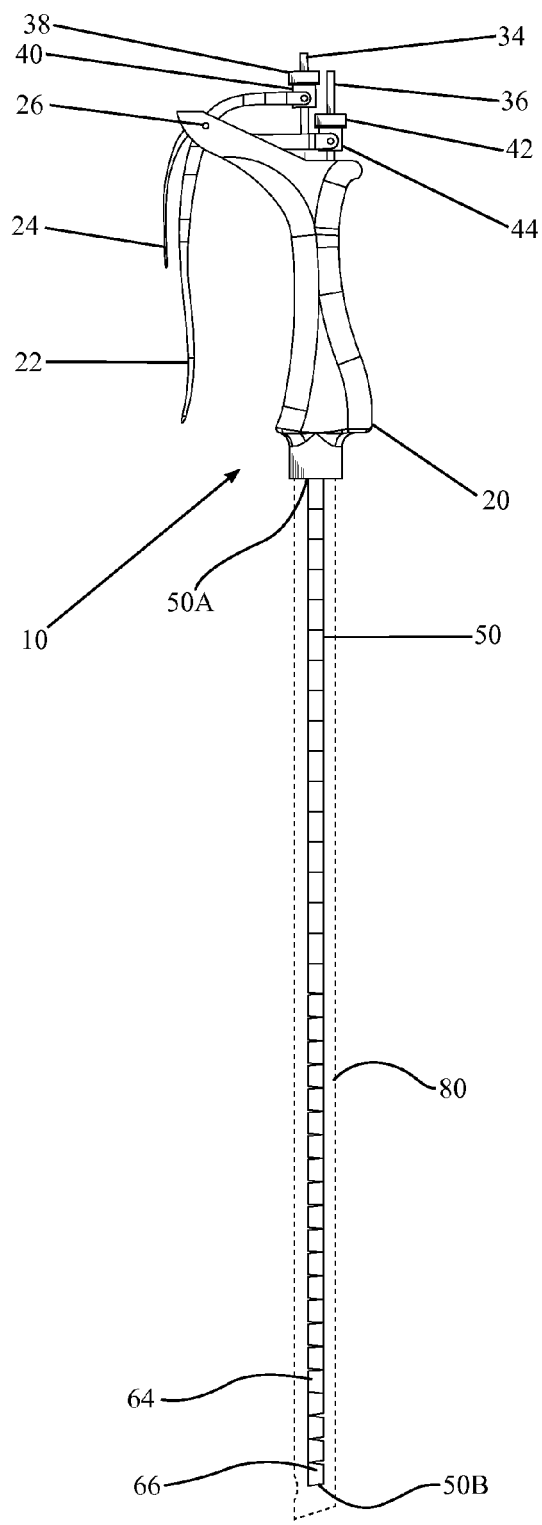
FIG. 2 is a side view of the manually articulatable intubation apparatus in which a stylet thereof is shown without any arcuations.

FIG. 2 shows the stylet 50 in a non-articulated state. In this regard, both the major handle lever 22 and the minor handle lever 24 are in static, neutral positions without being pulled toward the handle body 20. Further, the first and second tensioning thumb nuts 38, 42 have been adjusted so that that an initial tension in the first and second filaments 74, 76 is minimal. Thus, the stylet 50 extends straight below the handle body 20 without any significant arcuation present in the stylet 50, and thus there is no bending of the endotracheal tube 80.

Figure 3:
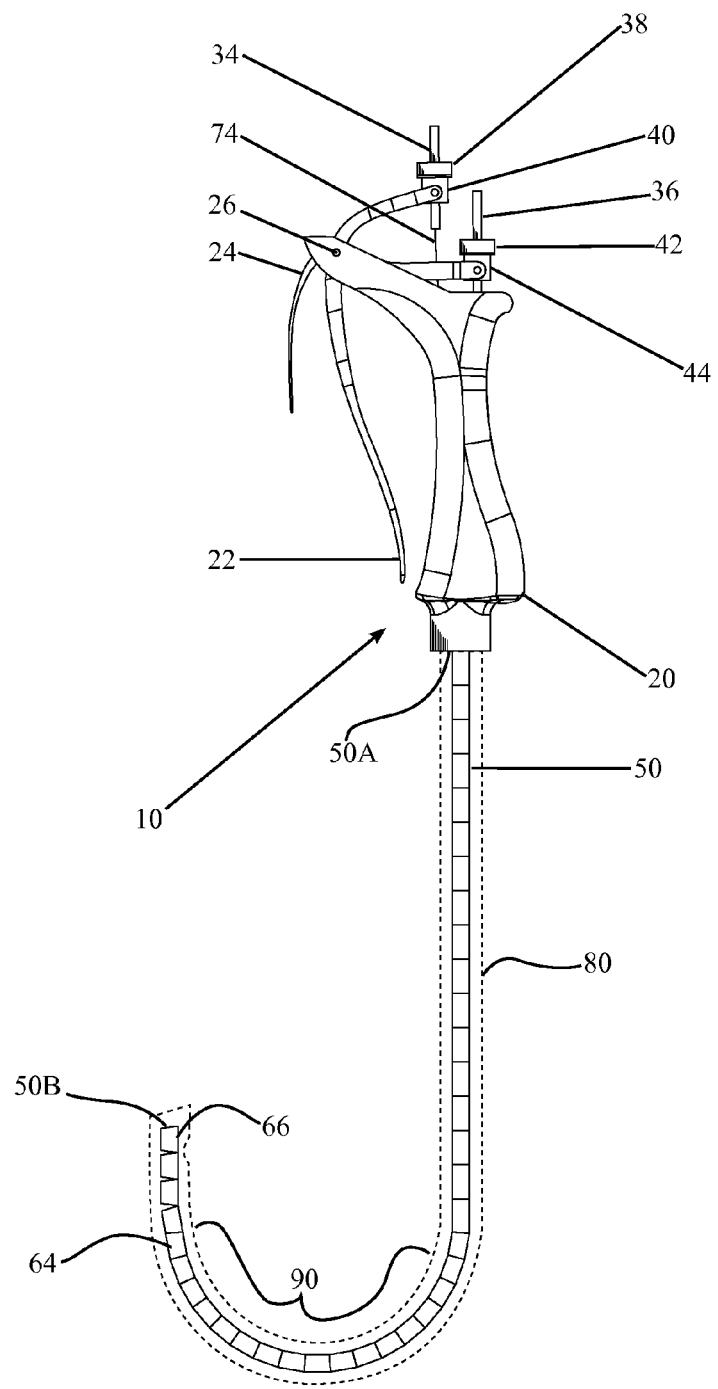
FIG. 3 is a side view of the manually articulatable intubation apparatus in which the stylet thereof is shown with a primary arcuation.

FIG. 3 shows the stylet 50 in a first articulated state. In this regard, the major handle lever 22 has been pulled toward the handle body 20 while the minor handle lever 24 remains in a static, neutral position without being pulled toward the handle body 20. Pulling the major handle lever 22 toward the handle body 20 pivots the major handle lever 22 on the axle pin 28 lifting the first gimbal and tensioning assembly connecting the first filament 74 to the major handle lever 22 thereby placing the first filament 74 under tension (or increased tension if already under initial tension as a result of adjustment to the first tensioning thumb nut 38). The tension (or increased tension) in the first filament 74 places the stylet 50 under compression (or increased compression) from the first location 64 toward the first end 50A. The compressive forces result in the stylet 50 acquiring a primary arcuation 90 extending from the first location 64 toward the first end 50A of the stylet 50. The degree of curvature of the primary arcuation 90 may be varied by varying the position of the major handle lever 22 as well as turning the first tensioning thumb nut 38. Releasing the major handle 22 to return to its static, neutral position allows the primary arcuation 90 to be released from the stylet 50, for example, during withdrawal of the stylet 50 from the lumen of the endotracheal tube. When articulated into the primary arcuation 90, portions of the stylet 50 corresponding with the primary arcuation 90 press against the interior sidewall of the endotracheal tube 80 forcing the endotracheal tube 80 to conform with the primary arcuation 90.

Figure 4:
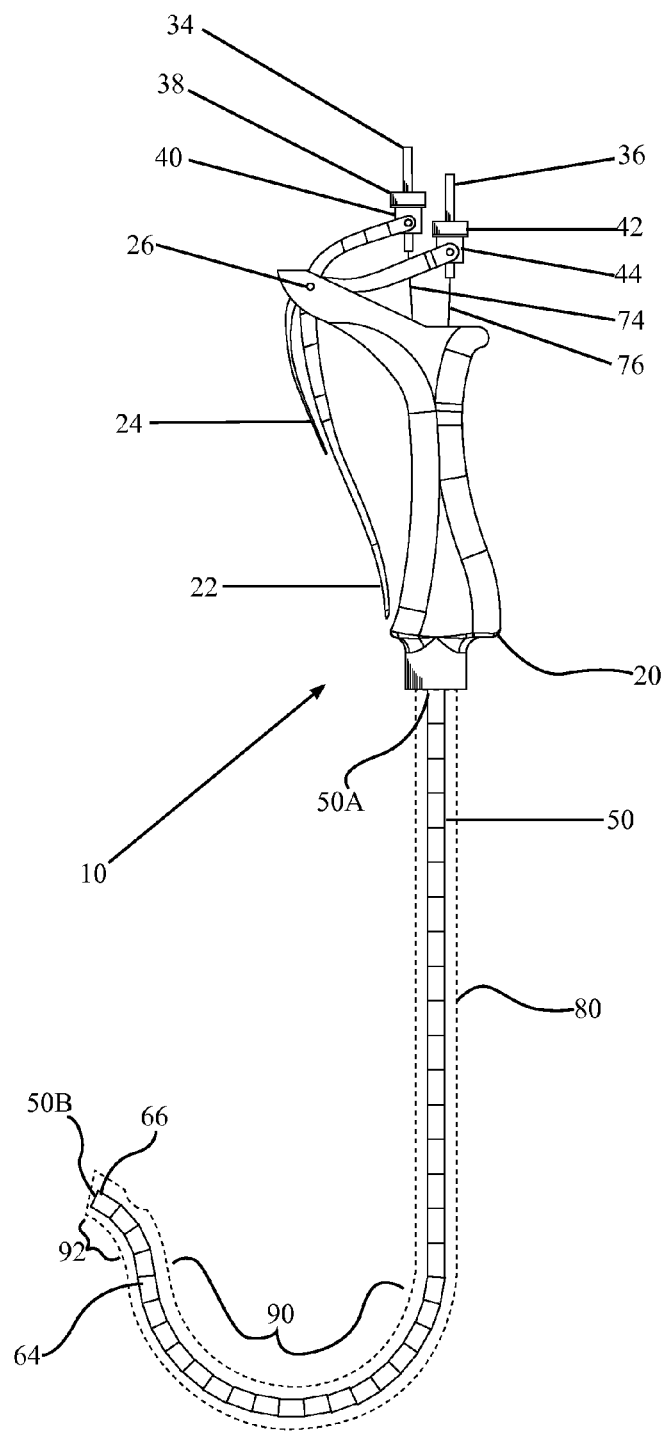
FIG. 4 is a side view of the manually articulatable intubation apparatus in which the stylet thereof is shown with a primary arcuation and a secondary arcuation.

FIG. 4 shows the stylet 50 in a second articulated state. In this regard, both the major handle lever 22 and the minor handle lever 24 have been pulled toward the handle body 20. As more fully described elsewhere herein, pulling the major handle lever 22 articulates the stylet 50 into the primary arcuation 90, with the endotracheal tube 80 bending in conformance with the primary arcuation 92. Pulling the minor handle 24 toward the handle body 20 pivots the minor handle lever 22 on the axle pin 28 lifting the second gimbal and tensioning assembly connecting the second filament 76 to the minor handle lever 24 thereby placing the second filament 76 under tension (or increased tension if already under initial tension as a result of adjustment to the second tensioning thumb nut 42). The tension (or increased tension) in the second filament 76 places the stylet 50 under compression (or increased compression) from the second location 66 toward the first location 64. The compressive forces result in the stylet 50 acquiring a secondary arcuation 92 extending from the second location 66 toward the first location 64 of the stylet 50. The degree of curvature of the secondary arcuation 92 may be varied by varying the position of the minor handle lever 24 as well as turning the second tensioning thumb nut 42. Releasing the minor handle 24 to return to its static, neutral position allows the secondary arcuation 92 to be released from the stylet 50, for example, during withdrawal of the stylet 50 from the lumen of the endotracheal tube. When articulated into the secondary arcuation 92, portions of the stylet 50 corresponding with the secondary arcuation 92 press against the interior sidewall of the endotracheal tube 80 forcing the endotracheal tube 80 to conform with the secondary arcuation 92.

Figure 5:
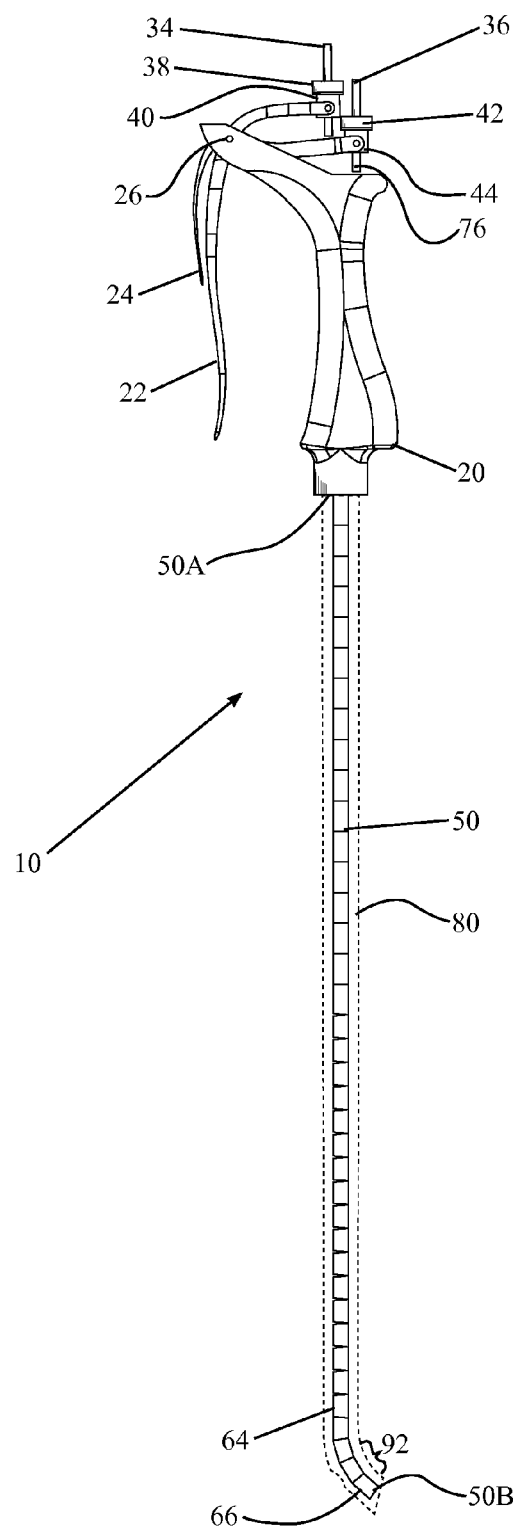
FIG. 5 is a side view of the manually articulatable intubation apparatus in which the stylet thereof is shown with a secondary arcuation.

FIG. 5 shows the stylet 50 in a third articulated state. In this regard, only the minor handle lever 24 has been pulled toward the handle body 20 while the major handle lever 22 remains in a static, neutral position without being pulled toward the handle body 20. As more fully described elsewhere herein, pulling the minor handle lever 24 articulates the stylet 50 into the secondary arcuation 92, with the endotracheal tube 80 bending in conformance with the secondary arcuation 92.

Depending upon which of the major and minor handle levers 22, 24 are pulled, the stylet 50 may be varied among a non-articulated state without any arcuation, the first articulated state with only the primary arcuation 90 present, the second articulated state with both the primary arcuation 90 and secondary arcuation 92 present, and the third articulated state with only the secondary arcuation 92 present. Further, the degree of curvature of both the primary and secondary arcuations 90, 92 can be varied as desired, and the stylet 50 can be provided with the secondary arcuation 92 independent of the presence of the primary arcuation 90 and with the primary arcuation 90 independent of the presence of the secondary arcuation 92.

Figure 6:
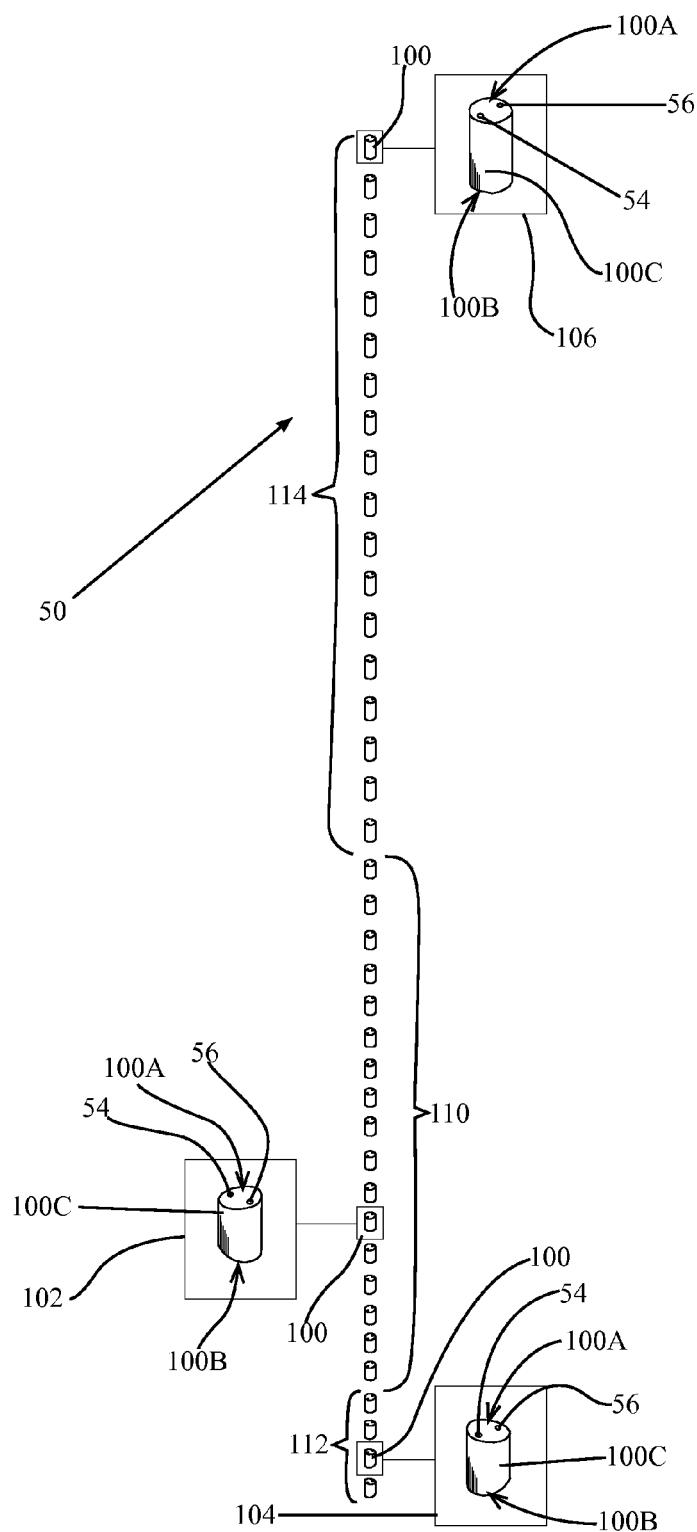
FIG. 6 is an exploded perspective view of one embodiment of a stylet of the manually articulatable intubation apparatus.

FIG. 6 shows one embodiment of the articulating stylet 50 in an exploded view. The articulating stylet 50 is comprised of a plurality of individual beads 100. Beads 100 in different positions along the longitudinal extent of the stylet 50 may have different configurations. For example, some of the beads 100 may be configured like the individual bead 100 shown in the enlarged view outlined by box 102, other beads 100 may be configured like the individual bead 100 shown in the enlarged view outlined by box 104, and other beads 100 may be configured like the individual bead 100 shown in the enlarged view outlined by box 106.

Regardless of their configuration, each individual bead 100 may have the first and second longitudinal passageways 54, 56 formed therethrough permitting passage of the first and second filaments 74, 76 within the stylet 50. The first passageway 54 and second passageway 56 may be formed at first and second radial locations near the outer surface of an individual bead 100. In this regard, the first and second radial locations of the first and second passageways 54, 56 may be separated by about 180 degrees measured around the circumference of the bead 100 resulting in the first and second filaments 74, 76 being near the outer surface of the stylet 50 but on opposite sides of a cross-sectional diameter of the stylet 50. In other embodiments, one or more of the individual beads 100 may be provided with only a single passageway through which both of the first and second filaments 74, 76 extend.

The stylet 50 may be comprised of various series of differently configured individual beads 100. For example, there may be a first series 110 of beads 100 configured like the beads 100 shown in box 102, a second series 112 of beads 100 configured like the beads 100 shown in box 104, and a third series 110 of beads 100 configured like the beads 100 shown in box 106. The first series 110 of beads 100 may comprise a portion of the stylet 50 that may be articulated into the primary arcuation 90, the second series 112 of beads 100 may comprise a portion of the stylet 50 that may be articulated into the secondary arcuation 92, and the third series 112 of beads 100 may comprise a non-articulated portion of the stylet 50 between the primary arcuation 90 and the first end 50A of the stylet 50.

As illustrated in the enlarged view of box 106, each bead 100 included in the third series 114 of beads 100 includes flat top and bottom end surfaces 100A, 100B that are perpendicular or near perpendicular to the side surface 100C of the bead 100. As illustrated in the enlarged view of boxes 102 and 104, each bead 100 included in the first series 110 and second series 112 of beads 100 includes top and bottom end surfaces 100A, 100B that are at non-perpendicular angles with respect to the side surface 100C of the bead 100, providing the beads 100 of the first series 110 of beads 100 and second series 112 of beads 100 with angled or beveled end surfaces 100A, 1008. In this regard, angling or beveling of the top and bottom end surfaces 100A, 100B of the beads 100 in the first and second series 110, 112 of beads 100 facilitates articulation of the stylet 50 into the respective primary and secondary arcuations 90, 92 in response to tension in the respective first and second filaments 74, 76 received in the respective first and second passageways 54, 56 by providing the stylet 50 with portions where compressive forces resulting from tension in the first and second filaments 74, 76 effectively shorten the length of the stylet 50 (on the inside of the curve of the respective primary and secondary arcuations 90, 92) by bringing the top and bottom end surfaces 100A, 100B of adjacent beads 100 in closer proximity. Further, the degree to which the end surfaces 100A, 1008, of the beads in the first series 110 of beads 100 and the second series 112 of beads 100 are angled with respect to the side surfaces 100C of the beads 100 may be varied to control the amount of curvature in the primary and secondary arcuations 90, 92. For example, the end surfaces 100A, 1008 of the beads 100 included in the first series of beads 110 may be angled such that the stylet 50 may be articulated into a primary arcuation 90 having a radius of approximately 2.5 inches.

In other embodiments, such as for example where the stylet 50 is not comprised of individual beads 100 but rather a continuous longitudinal extent of material, notches or the like formed in the side surface of the stylet 50 may be provided to achieve a similar result. Additionally, in other embodiments, one or more of the beads 100 in the first and/or second series 110, 112 of beads 100 many have only one or no angled or beveled end surfaces 100A, 1008.

As can be seen by comparing the enlarged views of boxes 102 and 104, the end surfaces 100A, 1008 of the beads 100 in the first series 110 may be angled such that the length of the side surface 100C of the bead 100 proximal to the first passageway 54 is shorter in length than the side surface 100C of the bead 100 proximal to the second passageway 56, and the end surfaces 100A, 1008 of the beads 100 in the second series 112 may be angled such that the length of the side surface 100C of the bead 100 proximal to the second passageway 56 is shorter in length than the side surface 100C proximal to the first passageway 54. Essentially, the angled end surfaces 100A, 100B of the beads 100 included in the second series of beads 112 may be oriented in an opposite direction to that of the end surfaces 100A, 1008 in the first series of beads 110. Angling of the end surfaces 100A, 100B of the beads 100 included in the second series of beads 112 in an orientation opposite that of the end surfaces 100A, 1008 in the first series of beads 110 facilitates the secondary arcuation 92 of the stylet 50 being oriented in an opposing direction to that of the primary arcuation 90.

Figure 7:
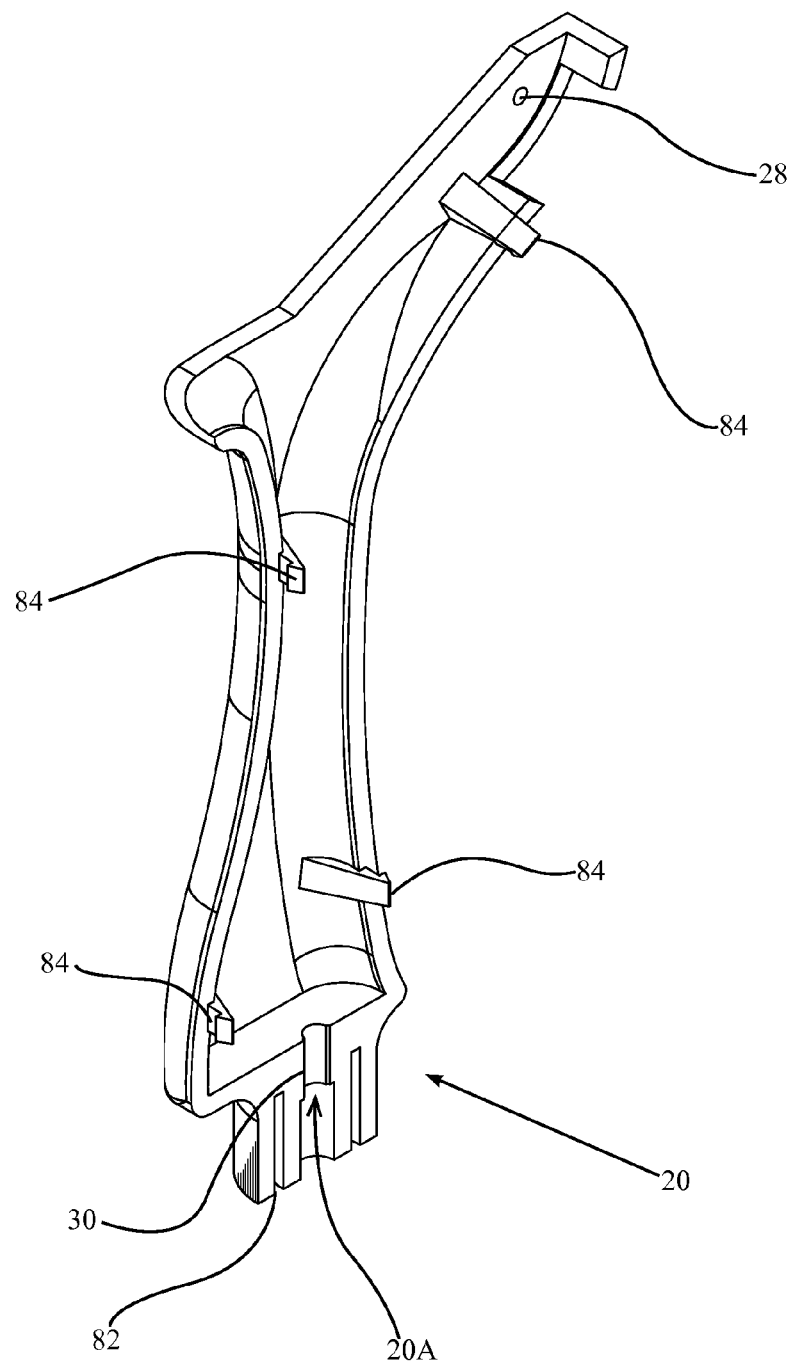
FIG. 7 is a perspective cross-sectional view of one-half of one embodiment of a handle body of the manually articulatable intubation apparatus.

FIG. 7 shows a perspective cross-sectional view of one-half of one embodiment of a handle body 20 of the manually articulatable intubation apparatus 10. The other half of the handle body 20 may be configured in a similar manner.

The handle body 20 includes an endotracheal tube slot 82 at the base of the handle body 20. The endotracheal tube slot 82 may be configured to receive an endotracheal tube adaptor on the proximal end of an endotracheal tube 80 to secure a proximal end of the endotracheal tube 80 to the handle body 20 during use of the manually articulatable intubation apparatus 10 such as depicted in FIG. 2, 3, 4, or 5. In this regard, the endotracheal tube slot 82 may be large enough to accept a standard endotracheal tube adaptor, and small enough to hold it fixed. In this regard, a width of the endotracheal tube slot 82 may be such that the endotracheal tube adaptor may be press fit into the slot 82 to retain the tube 80 in proximity with the handle body 20 during insertion of the tube 80 into a patient's airway while articulating the stylet 50 disposed within the lumen of the tube 80. Upon proper positioning of the endotracheal tube 80 within the patient's airway, the endotracheal tube adaptor may be removed from the endotracheal tube slot 82 of the handle body 20 as the stylet 50 is withdrawn from the interior of the tube 80.

The handle body 20 also includes a stylet changing opening 30 at the base of the handle body 20. The first and second filaments 74, 76 (not shown in FIG. 7) extend through the stylet changing opening 30. In this regard, the stylet changing opening 30 may be smaller in diameter than a diameter of the first end 50A of the stylet 50. The stylet seating surface 20A extends outwardly from the bottom edge of the stylet changing opening 30 and provides the surface against which the first end 50A of the stylet 50 may be seated during using of the manually articulated intubation apparatus 10. The handle body 20 may extend below the stylet seating surface 20A to provide an opening that receives a portion of the proximal end of the stylet 50 thereby stabilizing the first end 50A of the stylet 50.

The stylet changing opening 30 provides an opening in the handle body 20 to feed the first and second threaded tensioning screws 34, 36 for initial assembly and future replacement of the stylet 50. In this regard, the stylet changing open 30 may have a diameter that is sufficient for passage of the first and second threaded tensioning screws 34, 36 therethrough. This allows for changing of the stylet 50. In this regard, the first and second filaments 74, 76 may be disconnected from the respective major and minor handle levers 22, 24 (e.g., by loosening the first and second tensioning thumb nuts 38, 42 until disengaged from the threads of the first and second threaded tensioning screws 34, 36) and the stylet 50 may be pulled away from the handle body 20 until the first and second threaded tensioning screws 34, 36 pass through the stylet changing opening 30. Thereafter, first and second threaded tensioning screws 34, 36 connected to first and second filaments 74, 76 of another stylet 50 may be passed through the stylet changing opening 30, through the open interior of the handle body 20, out of the top slot 32 of the handle body 20, through the respective first and second gimbals 40, 42 and connected to the respective major and minor handle levers 22, 24 by tightening the respective first and second tensioning thumb nuts 38, 42 onto the respective first and second threaded tensioning screws 34, 36.

The handle body 20 also includes a plurality of snap hooks 84 along the inside perimeter of the handle body 20 half. During assembly, the snaps hooks 84 may be received in corresponding snap hook retainers on the other half of the handle body 20 in order to retain the two halves of the handle body 20 together. The snap hooks 84 and their corresponding snap hook retainers may be made of the same material as the rest of the handle body 20. In this regard, the handle body 20 may be prepared by a single casting, by injection molding, and/or by machining. The material comprising the handle body 20 may be sufficiently hard to withstand the forces of repeated use and shall be elastic enough to inhibit cracking during normal use.

Deviations may be made from the specific embodiments disclosed in the specification without departing from the spirit and scope of the invention. The illustrations and discussion herein has only been provided to assist the reader in understanding the various aspects of the present disclosure. While this disclosure contains many specifics, these should not be construed as limitations on the scope of the disclosure or of what may be claimed, but rather as descriptions of features specific to particular embodiments of the disclosure. Certain features that are described in this specification in the context of separate embodiments and/or arrangements can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Additionally, the foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An apparatus useful in the positioning of an endotracheal tube within an airway, said apparatus comprising:
    a stylet having a first end and a second end, said second end being insertable within a lumen of the endotracheal tube such that at least a portion of a longitudinal extent of said stylet is received within the lumen of the endotracheal tube;
    a first filament extending substantially parallel with a longitudinal axis of said stylet, said first filament being connected to said stylet at a first location between said first and second ends;
    a second filament extending substantially parallel with said longitudinal axis of said stylet, said second filament being connected to said stylet at a second location farther from said first end than said first location;
    a first tensioning mechanism operable to put said first filament under tension to articulate said stylet into a primary arcuation extending from said first location toward said first end, wherein said first tensioning mechanism comprises a first lever pivotable about a fulcrum, said first filament being connected to said first lever;
    a second tensioning mechanism operable to put said second filament under tension to articulate said stylet into a secondary arcuation extending from said second location toward said first location, wherein said second tensioning mechanism comprises a second lever pivotable about a fulcrum, said second filament being connected to said second lever;
    a first gimbal and first tension adjustment assembly connecting said first filament to said first lever; and
    a second gimbal and second tension adjustment assembly connecting said second filament to said second lever.

2. The apparatus of claim 1 wherein said second location coincides with said second end.

3. The apparatus of claim 1 wherein said second location is between said first location and said second end.

4. The apparatus of claim 1 wherein said primary arcuation and said secondary arcuation are oriented in opposing directions.

5. The apparatus of claim 1 wherein said primary arcuation and said secondary arcuation are substantially co-planar.

6. The apparatus of claim 1 further comprising:
    an internal passageway extending longitudinally within said stylet from said first end to said second location, wherein both of said first and second filaments are receivable in said internal passageway.

7. The apparatus of claim 1 further comprising:
    a first internal passageway extending longitudinally within said stylet from said first end to said first location, wherein said first filament is receivable in said first internal passageway; and
    a second internal passageway extending longitudinally within said stylet from said first end to said second location, wherein said second filament is receivable in said second internal passageway.

8. The apparatus of claim 7 wherein said first internal passageway is proximal to an outer surface of said stylet at a first radial location relative to said longitudinal axis of said stylet, and wherein said second internal passageway is proximal to an outer surface of said stylet at a second radial location relative to said longitudinal axis of said stylet.

9. The apparatus of claim 8 wherein said first and second radial locations are separated by about 180 degrees.

10. The apparatus of claim 1 wherein said first tensioning mechanism and said second tensioning mechanism are independently operable from one another.

11. The apparatus of claim 1 further comprising a handle body, said handle body including a surface against which said first end of said stylet is seated, said handle body supporting at least one axle pin providing the fulcrums about which at least one of said first and second levers are pivotable.

12. The apparatus of claim 1 wherein said first gimbal and first tension adjustment assembly adjust an initial tension on said first filament, and wherein said second gimbal and second tension adjustment assembly adjust an initial tension on said second filament.

13. The apparatus of claim 1 wherein said first gimbal and first tension adjustment assembly permits disconnection of said first filament from said first lever and reconnection of said first filament to said first lever, and wherein said second gimbal and second tension adjustment assembly permits disconnection of said second filament from said second lever and reconnection of said second filament to said second lever.

14. The apparatus of claim 1 wherein said stylet comprises a plurality of individual beads.

15. The apparatus of claim 14 wherein said plurality of individual beads includes a primary series of beads and a secondary series of beads, wherein said primary series of beads corresponds with said primary arcuation and wherein said secondary series of beads corresponds with said secondary arcuation.

16. The apparatus of claim 15 wherein at least one of said beads comprising said primary series of beads includes at least one beveled end surface, and wherein at least one of said beads comprising said secondary series of beads includes at least one beveled end surface.

17. The apparatus of claim 1 wherein said stylet includes a plurality of individual notches formed therein.

18. The apparatus of claim 17 wherein said plurality of individual notches includes a primary series of notches and a secondary series of notches, wherein said primary series of notches are formed in a portion of a lengthwise extent of said stylet corresponding with said primary arcuation and wherein said secondary series of notches are formed in a portion of a lengthwise extent of said stylet corresponding with said secondary arcuation.

19. An apparatus useful in the positioning of an endotracheal tube within an airway, said apparatus comprising:
    a stylet having a first end and a second end, said second end being insertable within a lumen of the endotracheal tube such that at least a portion of a longitudinal extent of said stylet is received within the lumen of the endotracheal tube;
    said stylet comprising at least a first articulatable portion extending toward said first end from a first location along a longitudinal extent of said stylet and a second articulatable portion extending toward said first location from a second location along the longitudinal extent of the stylet farther from said first end than said first location, said first articulatable portion of said stylet being articulatable into a primary arcuation and said second articulatable portion of said stylet being articulatable into a secondary arcuation, said first and second articulatable portions of said stylet being independently articulatable into respective said primary and secondary arcuations;
    a first articulating mechanism operable to articulate said first portion of said stylet into said primary arcuation, wherein said first articulating mechanism comprises:
        a first filament extending substantially parallel with a longitudinal axis of said stylet, said first filament being connected to said stylet at said first location;
        a first lever pivotable about a fulcrum; and
        a first gimbal and first tension adjustment assembly connecting said first filament to said first lever;
    a second articulating mechanism operable to articulate said second portion of said stylet into said secondary arcuation, wherein said second articulating mechanism comprises:
        a second filament extending substantially parallel with said longitudinal axis of said stylet, said second filament being connected to said stylet at said second location;
        a second lever pivotable about a fulcrum; and
        a second gimbal and second tension adjustment assembly connecting said second filament to said second lever.

20. The apparatus of claim 19 wherein said second location coincides with said second end.

21. The apparatus of claim 19 wherein said second location is between said first location and said second end.

22. The apparatus of claim 19 wherein said primary arcuation and said secondary arcuation are oriented in opposing directions.

23. The apparatus of claim 19 wherein said primary arcuation and said secondary arcuation are substantially co-planar.

24. The apparatus of claim 19 further comprising:
    an internal passageway extending longitudinally within said stylet from said first end to said second location, wherein both of said first and second filaments are receivable in said internal passageway.

25. The apparatus of claim 19 further comprising:
    a first internal passageway extending longitudinally within said stylet from said first end to said first location, wherein said first filament is receivable in said first internal passageway; and
    a second internal passageway extending longitudinally within said stylet from said first end to said second location, wherein said second filament is receivable in said second internal passageway.

26. The apparatus of claim 25 wherein said first internal passageway is proximal to an outer surface of said stylet at a first radial location relative to said longitudinal axis of said stylet, and wherein said second internal passageway is proximal to an outer surface of said stylet at a second radial location relative to said longitudinal axis of said stylet.

27. The apparatus of claim 26 wherein said first and second radial locations are separated by about 180 degrees.

28. The apparatus of claim 19 further comprising a handle body, said handle body including a surface against which said first end of said stylet is seated, said handle body supporting at least one axle pin providing the fulcrums about which at least one of said first and second levers are pivotable.

29. The apparatus of claim 19 wherein said first gimbal and first tension adjustment assembly adjusts an initial tension on said first filament, and wherein said second gimbal and second tension adjustment assembly adjusts an initial tension on said second filament.

30. The apparatus of claim 19 wherein said first gimbal and first tension adjustment assembly permits disconnection of said first filament from said first lever and reconnection of said first filament to said first lever, and wherein said second gimbal and second tension adjustment assembly permits disconnection of said second filament from said second lever and reconnection of said second filament to said second lever.

31. The apparatus of claim 19 wherein said stylet comprises a plurality of individual beads.

32. The apparatus of claim 31 wherein said plurality of individual beads includes a primary series of beads and a secondary series of beads, wherein said primary series of beads comprises said first articulatable portion of said stylet, and wherein said secondary series of beads comprises said second articulatable portion of said stylet.

33. The apparatus of claim 32 wherein at least one of said beads comprising said primary series of beads includes at least one beveled end surface, and wherein at least one of said beads comprising said secondary series of beads includes at least one beveled end surface.

34. The apparatus of claim 19 wherein said stylet includes a plurality of individual notches formed therein.

35. The apparatus of claim 34 wherein said plurality of individual notches includes a primary series of notches and a secondary series of notches, wherein said primary series of notches are formed in said first articulatable portion of said stylet, and wherein said secondary series of notches are formed in said second articulatable portion of said stylet.

* * * * *

UNITED STATES PATENT AND TRADEMARK OFFICE
CERTIFICATE OF CORRECTION

PATENT NO.         : 9,010,320 B2
APPLICATION NO.    : 13/794121
DATED              : April 21, 2015
INVENTOR(S)        : William Furman et al.

Page 1 of 1

It is certified that error appears in the above-identified patent and that said Letters Patent is hereby corrected as shown below:

In the Specification

Column 9, line 30, delete "1008" and insert therefore -- 100B --.

Column 9, line 44, delete "1008" and insert therefore -- 100B --.

Column 9, line 49, delete "1008" and insert therefore -- 100B --.

Column 9, line 60, delete "1008" and insert therefore -- 100B --.

Column 9, line 62, delete "1008" and insert therefore -- 100B --.

Column 9, line 67, delete "1008" and insert therefore -- 100B --.

Column 10, line 7, delete "1008" and insert therefore -- 100B --.

Column 10, line 10, delete "1008" and insert therefore -- 100B --.

Column 10, line 24, delete "FIG." and insert therefore -- FIGS. --.

Signed and Sealed this
Eighteenth Day of August, 2015

Michelle K. Lee
*Director of the United States Patent and Trademark Office*